(12) United States Patent
Khalafpour et al.

(10) Patent No.: US 7,534,333 B2
(45) Date of Patent: May 19, 2009

(54) ELECTROCHEMICAL GAS SENSOR

(75) Inventors: Peyman Khalafpour, Alberta (CA); Stuart Christopher Cutler, Hampshire (GB)

(73) Assignee: City Technology Limited, Portsmouth (GB)

( * ) Notice: Subject to any disclaimer, the term of this patent is extended or adjusted under 35 U.S.C. 154(b) by 895 days.

(21) Appl. No.: 11/138,157

(22) Filed: May 26, 2005

(65) Prior Publication Data

US 2006/0266647 A1    Nov. 30, 2006

(51) Int. Cl.
*G01N 27/413* (2006.01)
(52) U.S. Cl. ............... 204/431; 204/430; 204/432
(58) Field of Classification Search .............. None
See application file for complete search history.

(56) References Cited

U.S. PATENT DOCUMENTS

| | | | | |
|---|---|---|---|---|
| 4,406,770 A | * | 9/1983 | Chan et al. | 204/406 |
| 4,824,551 A | * | 4/1989 | Rupich | 204/431 |
| 6,099,708 A | * | 8/2000 | Mallory et al. | 204/412 |
| 2002/0121438 A1 | * | 9/2002 | Saffell et al. | 204/415 |

* cited by examiner

*Primary Examiner*—Kaj K Olsen
*Assistant Examiner*—Kourtney R Salzman

(57) ABSTRACT

An electrochemical gas sensor which comprises an electrode assembly, including a catalytic sensing electrode and a counter electrode, mounted inside a housing provided with at least one gas entrance, a reservoir for containing electrolyte in use, a compressible wick for supplying the electrode assembly with electrolyte and a wick compression component. A first end of the wick extends into the reservoir and a second end of the wick contacts the electrode assembly. The wick compression component compresses the wick in a direction substantially radial to an axis joining its first and second ends.

35 Claims, 7 Drawing Sheets

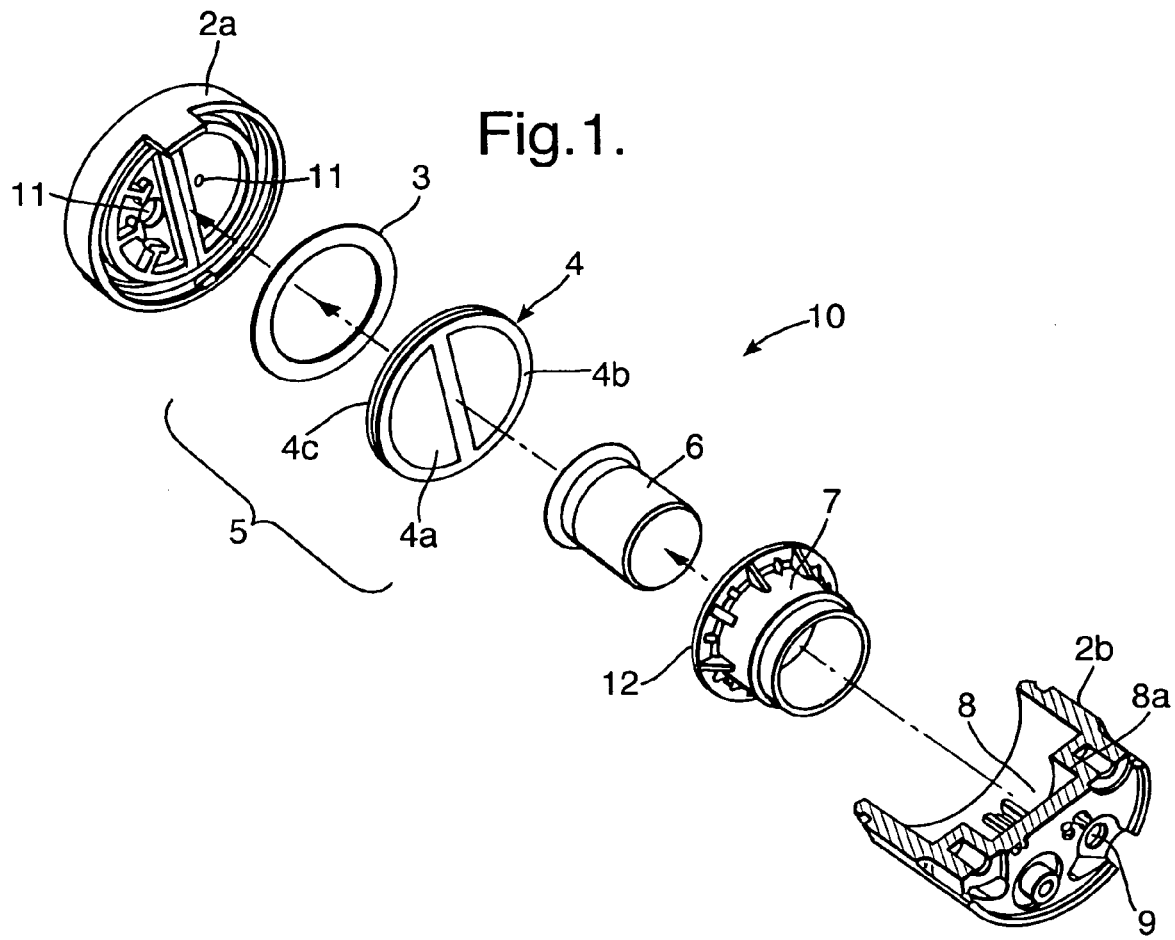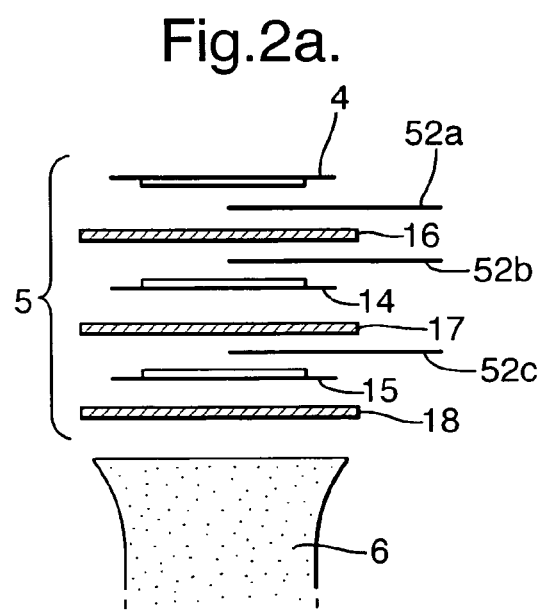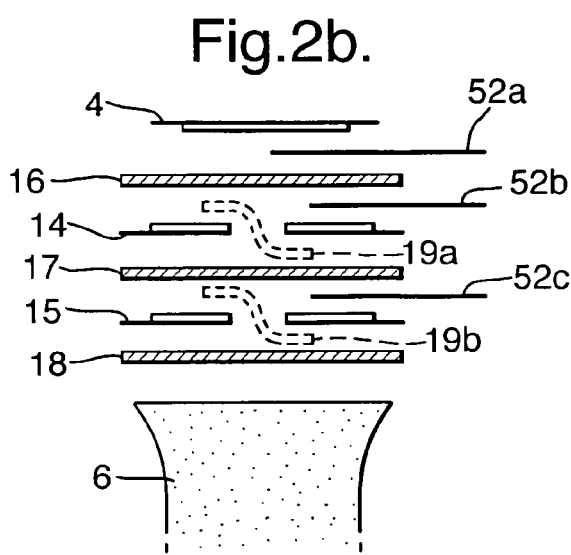

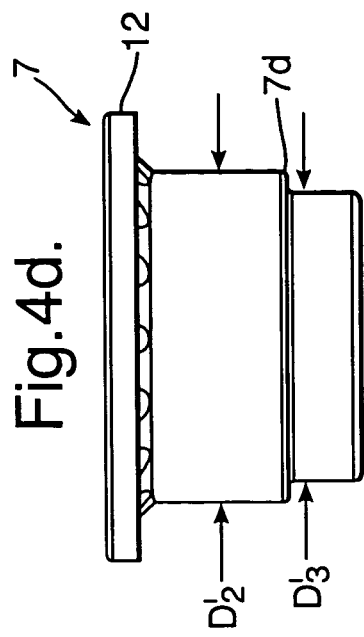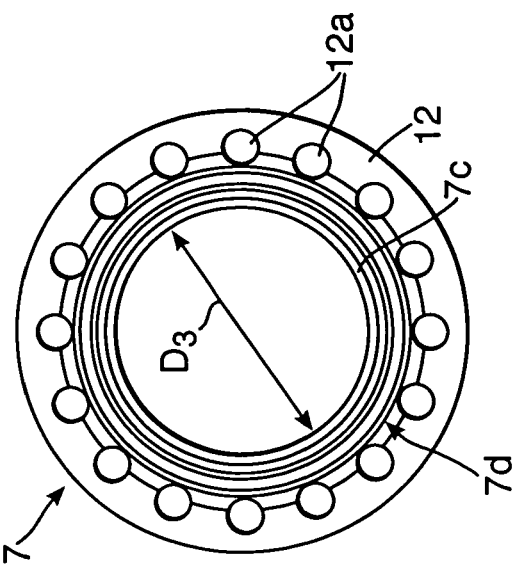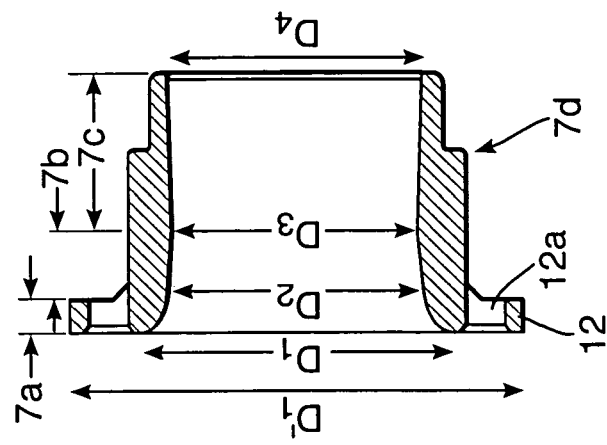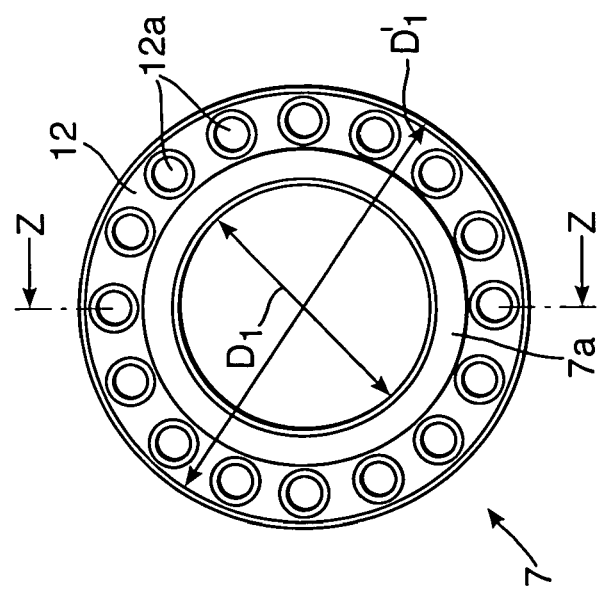

ELECTROCHEMICAL GAS SENSOR

This invention relates to an electrochemical gas sensor and a method for manufacturing the same.

Electrochemical gas sensors operate by oxidizing or reducing gases and vapours on a catalytic electrode, thereby producing an electric current which can be used as a measure of the concentration of gas or vapour in the surrounding atmosphere. Examples of such sensors are described in GB-A-2094005. In order for the oxidation or reduction reaction to take place, the catalytic electrode must be in contact with an electrolyte. In most cases, the electrolyte is in the form of a liquid. The reaction takes place at the interface between the electrode and the electrolyte, which further must be accessible by the target gas. Thus in order to work efficiently, the catalyst, the gas and the electrolyte must be in sufficient contact.

Contact is conventionally achieved by positioning the catalytic electrode adjacent to a separator which is wetted with and retains the electrolyte. Typically, an electrochemical sensor is provided with two additional electrodes; a reference electrode to whose potential the sensing electrode is referred and a counter electrode which completes the oxidation/reduction process by removing the ions produced as a result of the reaction occurring at the sensing electrode. All of the electrodes in this electrode assembly or 'stack' need to be in good contact with the electrolyte and as such additional separators are typically placed between the electrodes. The separators press against the electrodes and maintain liquid contact. The separators also prevent the electrodes and their accompanying current collectors from making contact with each other which could otherwise short circuit the cell internally. Shorting would not only inhibit the electrochemical reaction but would prevent the measurement of any current generated by the electrochemical process, effectively destroying the cell.

Typically, gas enters the sensor through a diffusion barrier, which may comprise a capillary disposed in the sensor housing. This controls the rate of gas entering and exiting the sensor. Access to the cell is further obstructed, to a lesser extent, by the electrodes themselves, which typically comprise a gas sensitive, catalytic material disposed on a (typically PTFE) membrane. The membrane is hydrophobic but porous, allowing vapour and gas in and out of the cell via the capillary hole but preventing the escape of liquid. However, water vapour can migrate in and out of the cell.

Most electrolytes are either strong acids or bases or inorganic salts and as such they will take up or release water depending on the humidity of the environment to which they are exposed. Thus, depending on the water balance of the electrolyte in the surrounding environment, water vapour may enter or exit the cell. In an environment of low relative humidity, this causes the sensor to dry out resulting in a loss of reaction activity and lengthened response times. To address this problem, sensors are typically provided with a reservoir of electrolyte to keep the separators, and hence the electrodes, wet even under dry ambient conditions. To this end, conventional reservoirs comprise a cavity in the body of the sensor containing electrolyte and are further provided with some form of wick which supplies electrolyte to the separators from the reservoir. Conventional wicking arrangements typically comprise an absorbent mat partly filling the reservoir cavity from which a glass fibre strip extends to the electrode assembly. Electrolyte migrates from the reservoir to the separators in the electrode assembly as a result of the physical properties of the materials which link the two locations. Alternatively, solid wicking components may be used which make use of the surface tension properties of the electrolyte to draw the liquid towards the separator.

However it has been found that electrochemical sensors made with conventional wicks tend to experience a loss in signal and increase in response time when the sensor is exposed to dry environments for prolonged periods. Investigation has shown that this is because the wicks do not transport electrolyte to the separators efficiently and thus allow the electrodes to become dry, even whilst electrolyte remains in the cell. What is needed is a more efficient technique for providing the electrodes with electrolyte.

An electrochemical gas sensor in accordance with the present invention comprises an electrode assembly, including a catalytic sensing electrode and a counter electrode, mounted inside a housing provided with at least one gas entrance, a reservoir for containing electrolyte in use, a wick for supplying the electrode assembly with electrolyte and a wick compression component, wherein a first end of the wick extends into the reservoir and a second end of the wick contacts the electrode assembly, and the wick compression component compresses the wick in a direction substantially radial to an axis joining its first and second ends.

A method of manufacturing an electrochemical sensor in accordance with the present invention comprises the steps of (A) compressing a wick having first and second ends in a direction substantially radial to an axis joining its first and second ends, (B) positioning the compressed wick such that the first end of the wick extends into a reservoir for containing electrolyte in use and the second end of the wick contacts an electrode assembly, including a catalytic sensing electrode and a counter electrode, inside a housing, the housing being provided with at least one gas entrance and (C) at least partially filling the reservoir with electrolyte such that the wick supplies the electrode with electrolyte from the reservoir.

By compressing the wick in this way, it has been found that the wicking efficiency is significantly improved. It is believed that this is the result of an enhanced capillary action effect, drawing the electrolyte along the length of the wick undersurface tension. The compressed wick allows a sensor to maintain its response speed in environments of low relative humidity over much longer periods of time than conventional sensors. Further, the use of a separate wick compression component helps to align the components within the housing to ensure good performance.

The wick could be compressed by any suitable component, such as a collar which fits around the wick and is subsequently tightened. Preferably however, the wick compression component has a longitudinal axis extending between a first open end adjacent to the reservoir and a second open end adjacent to the electrode assembly, and defines an internal volume into which the wick is placed in use, wherein the cross-sectional area of the internal volume in a plane perpendicular to the longitudinal axis is less than the cross-sectional area of the wick prior to its insertion into the wick compression component at at least one point along the longitudinal axis, so that the internal walls exert a compressive force on the wick.

This configuration results in a low part count and is straightforward to manufacture and use in the assembly of different sensors.

The internal volume of the wick compression component can have any desired shape. Preferably, the internal volume has a substantially circular cross-section but it is feasible for the volume to be square, polygonal or even irregular in cross-section. Typically, prior to compression, the wick is substantially cylindrical. Compression can be applied along the length of the wick or over just a portion, as desired.

In one embodiment, at least a first portion of the internal volume is substantially cylindrical, at least a first part of the wick compression component having parallel sided internal walls. Alternatively, at least a first portion of the internal volume defined by the wick compression component is substantially frustoconical, the wick compression component having a first part which has an internal width dimension which is larger at its first end than at its second end, the first end located towards the reservoir. Such a configuration has been found to improve supply of electrolyte to the separators. It is believed this is due to the degree of wick compression increasing towards the electrode assembly, which draws electrolyte in the same direction under increased capillary action. However, it is also important to have a large contact area between the end of the wick and the electrode assembly to allow for a sufficient rate of electrolyte transfer between the wick and separators. Therefore it is preferable that the frustoconical portion does not extend all the way to the (second) end of the wick compression component. In a particularly preferred embodiment, whether the first portion is cylindrical or frustoconical, a second portion of the internal volume defined by the wick compression component, adjacent to the second end of the wick compression component, has a cross-sectional area larger than that of the cylindrical first portion. This combines the benefits of increased capillary action with a larger contact area between the wick and electrode assembly. The second portion may be cylindrical, frustoconical or defined by curved walls, typically having an increased cross-section towards the electrode assembly. Whilst the degree of capillary action may be reduced in this locality, the proximity of the separators (which typically have a greater affinity for the electrolyte than does the wick) is such that electrolyte flow is maintained across the region.

The optimum degree of compression will depend upon the particular sensor configuration and wick material used but it has been found preferable that the wick compression component has an internal width dimension at at least one point along the longitudinal axis which is 17% less than the width of the wick prior to insertion. Where the wick compression component defines a cylindrical internal volume, the internal diameter of the tube is preferably 17% less than the diameter of the wick, prior to insertion. In other embodiments, the degree of compression may be anything greater than or equal to about 5%. Preferably, the wick is compressed by at least 10%, most preferably between 15% and 20%.

The wick and wick compression component typically extend into the reservoir although not necessarily to the same extent. The wick may take up a significant proportion of the reservoir volume, up to 100% in some embodiments. Preferably, the wick takes up between 10% and 80%, further preferably about 30%, of the reservoir volume. It is advantageous that the wick has a capacity for holding electrolyte at least equal to that of the reservoir. In this way, the wick can hold the major proportion, if not all, of the electrolyte in the sensor and so avoid the presence of unconstrained liquid. Additional space left in the reservoir, housing or wick itself allows for liquid expansion should the electrolyte take up water in a humid environment.

Advantageously, the wick compression component may further comprise a surface for supporting the electrode assembly inside the housing so that the wick compression component contacts at least a portion of the electrode assembly. The electrode support surface may be provided by an open end of the wick compression component or by a flange provided around its end. This acts as a firm platform or base onto which the electrode stack can be built, and avoids the need for a moulded floor feature to be introduced into the housing in order to support the electrodes. Preferably, the wick is inserted into the wick compression component in such a way that its second end extends out of the second open end of the wick compression component. This may only be by a short way but is nonetheless beneficial since it ensures electrolytic contact between the wick and electrode assembly and provides a sufficiently resilient support for the electrode assembly. When the sensor is constructed, the electrode stack compresses the unbound end of the wick not only allowing for tolerances in the exact dimensions of the rigid components but also leasing to a "mushroomed" (spreading out) effect at the top of the wick, thus further increasing the contact area between the wick and the electrode stack. Alternatively, the second end of the wick could be substantially flush with the second end of the tube so that both the end of the tube and the end of the wick contact the electrode assembly, but in some cases this may risk loss of electrolytic contact.

The wick could be constructed from a conventional wick material such as glass matting. However, advantageously, the wick comprises a porous material, which is preferably fibrous. The separation between the fibres draws the electrolyte along the length of the wick under surface tension. Preferably, the fibres of the wick material are orientated substantially parallel to the axis joining the first and second ends of the wick. This ensures that the fibres draw the liquid directly from the reservoir (at the first end) to the separator (at the second end). Preferably, the fibres define elongate, substantially parallel pores aligned with the fibres. Alternatively, the material may have interconnected, approximately equiaxed pores for example.

In selecting a wick material, both the microstructural properties of the material itself and the microstructural properties of the wick assembled from that material need to be taken into account. On a microstructural level, the material should not dissolve or otherwise react on contact with the electrolyte, and must retain its strength. A hydrophobic material may be selected. The assembled wick must, as a whole, be capable of absorbing and storing electrolyte, and should be resilient in both longitudinal and radial directions. A preferred material found to satisfy these criteria is polyethylene.

The housing could comprise one or several parts. Preferably, the housing comprises a base and a lid.

Conveniently, the reservoir is defined by interior walls of the housing. Typically the reservoir will be contained in the housing base.

Preferably, the electrode assembly further comprises a reference electrode. In order to supply the electrodes with electrolyte from the wick, the electrode assembly advantageously further includes at least one separator. This could be arranged to transport electrolyte through a hole in the centre of the base electrode layer, around the outside or in accordance with any other known techniques.

An example of an electrochemical gas sensor in accordance with the present invention will now be described with reference to the accompanying drawings in which:

FIG. 1 is an exploded view of a gas sensor showing the main components, other components are not shown for clarity;

FIGS. 2a and 2b schematically depict an exploded view of electrode assemblies, suitable for use in the gas sensor of FIG. 1, in cross-section;

FIGS. 4a, 4b, 4c and 4d show respectively a plan view, a cross-section, a view from underneath and a side view of the wick compression component depicted in FIGS. 3a and 3b;

Figure 3A:
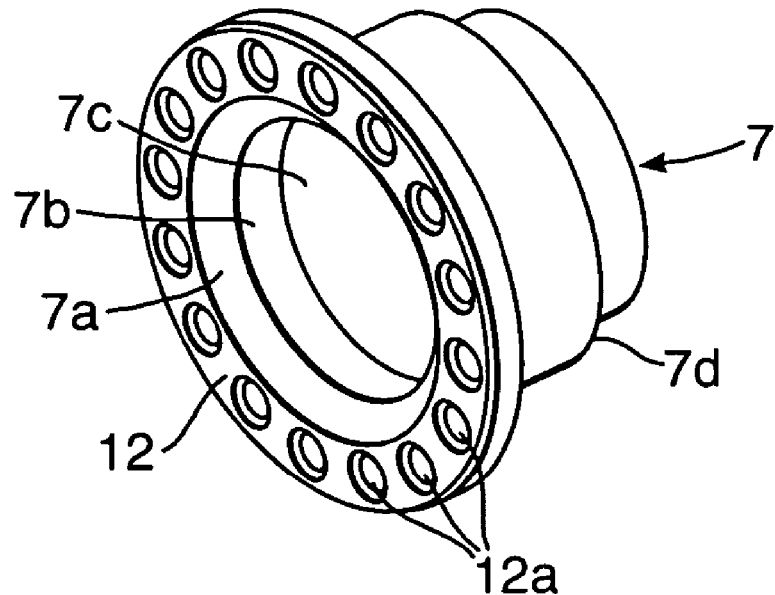
FIGS. 3a and 3b show perspective views of a wick compression component for use in a first embodiment of the invention.

The main functional components of an electrochemical gas sensor are shown in FIG. 1. Typically, all the components are disposed within a housing 2 comprising a lid 2a, provided with an aperture 11 for gas entry, and a base 2b which fits with the lid 2a to form an enclosure. The housing base 2b further defines a reservoir cavity 8 by means of internal walls 8a which, in use, is filled with electrolyte. Filling may be achieved after construction of the sensor by injection of electrolyte through a hole 9 in the housing base.

An electrode assembly 5 is disposed adjacent to the housing lid 2a to enable gas access to the electrodes. Typically, a diffusion barrier is provided which controls gas entry. This may be in the form of a diffusion-limiting membrane or the entry aperture 11 may be selected to be an appropriately sized capillary. More than one capillary may be provided in the lid 2a; for example, two capillaries 11 of different sizes are shown in FIG. 1. One or more filters 3 may also be provided between the gas entry 11 and the electrode 4 in the electrode stack 5 in order to remove substances from the ingressing gas which would otherwise interfere with the target gas reaction or damage the electrodes. Outboard filters may also be provided.

In its most basic form, the electrode assembly 5 may comprise only a sensing electrode 4 and counter electrode 15 (FIG. 2). Typically these take the form of a precious metal catalyst such as platinum black particles mounted on a porous backing tape. The target gas species reacts on the catalytic area, generating an electric current which is monitored by means of current collectors (not shown in FIG. 1), described below. The backing tape is typically a hydrophobic porous material such as PTFE.

The exemplary gas sensor depicted in FIG. 1 is a combined carbon monoxide and hydrogen sulphide sensor, and as such has two sensing electrodes, one adapted to detect each target gas, in the form of semicircular catalyst areas 4a and 4b mounted on a single circular backing 4c to form sensing electrode layer 4. However, the number of electrodes provided will depend on the gas sensor's application. Where a single gas is to be detected (such as CO, $H_2S$ or $SO_2$), a single sensing electrode may be provided by disposing only a single (circular) area of catalyst on the backing 4c.

It is preferable that the electrode assembly further includes a reference electrode. This and the counter electrode are omitted from FIG. 1 for clarity, but would be disposed in the electrode assembly 5 between the sensing electrode layer 4 and the wick 6. The reference and counter electrodes may be of a similar construction to the sensing electrode 4, although each electrode could employ a different catalyst. In some embodiments, different electrode designs may be selected, for example a solid reference electrode such as iridium/iridium oxide may be preferred. Further, whilst in this embodiment the catalysts are disposed on PTFE tapes, they could be provided on other backing materials. For example, the catalysts could be printed directly onto one or more of the separators, forming integrated electrode/separator components.

Two possible electrode configurations are shown in FIGS. 2a and 2b. In each case, a reference electrode 14 and a counter electrode 15 are provided between the sensing electrode 4 and the wick 6. Current collectors 52a, 52b and 52c are arranged to be in contact with the catalytic area on each of the electrodes.

In order to keep all the electrodes fully wetted, the electrode stack 5 conveniently further comprises one or more separators 16, 17, 18 which are disposed in the form of layers sandwiched between sensing electrode 3 and counter/reference electrode layer 4, and on the reservoir side of sensor layer 4. As shown in FIG. 2a, the separators may have a greater diameter than that of the electrodes 14 and 15 allowing them to meet at the sensor perimeter and thereby transport electrolyte around the edge of the electrodes 14 and 15. Alternatively, as shown in FIG. 2b, apertures could be provided in the middle of electrodes 14 and 15 and the separator layers 16, 17, 18 layers contact therethrough. Further alternatively, strips 19a, 19b of separator material could be arranged extending through such an aperture.

On the reservoir side, the sensor assembly 5 contacts a wick 6 which supplies the sensor assembly 5 with electrolyte from the reservoir. The wick 6 is typically made of a fibrous material orientated such that the fibres align approximately with the sensor axis and thus enhance the transport of electrolyte from the reservoir to the sensor stack 5.

The wick 6 is held in a wick compression component 7 which not only positions the wick inside the housing but also applies a substantially radial compressive force to the wick material. This is achieved by means of the wick compression component 7 having a smaller internal cross-section than that of the wick 6 prior to its insertion into the wick compression component 7. As will be described in more detail below, the wick compression component can take a number of forms, but in each case, the wick should be compressed by the wick compression component 7 at at least one point along its length. It has been found that this results in enhanced electrolyte transfer.

The wick compression component 7 also performs a number of other functions inside the sensor. For example, in this embodiment, the wick compression component 7 is provided with a flange 12 around one end which provides a support surface for the electrode assembly 5. This avoids the need for a support ledge to be provided in the sensor housing for this purpose. It is beneficial however if the wetted area of the electrode assembly is supported by the wick itself, to maintain electrolytic contact. In this case, the flange 12 provides support to the assembly via the wick 6 and at the perimeter.

As shown in FIG. 1, the wick is typically substantially cylindrical, both prior to insertion and after compression (but having a reduced diameter). As such, the wick 6 and wick compression component 7 typically have circular cross-sections in the direction perpendicular to their length, but they could take any other convenient shape. However, it is preferable that the wick compression component 7 exerts a uniform radial compression on the wick 6, and the use of a circular cross-section is a convenient way of achieving this.

To optimise the storage and transport of electrolyte within the sensor cell, the wick 6 typically extends some way into the reservoir 8. In some embodiments, the whole of the reservoir 8 may be filled by the wick. In other embodiments, it is generally preferred that at least 10% of the reservoir 8 is taken up by the wick so as to ensure adequate contact between the wick and electrolyte. In other cases, a greater percentage of the reservoir 8 may be filled by the wick 6, for example 30% or up to 80%. In order to avoid quantities of free liquid being present in the sensor, the wick 6 should have sufficient capacity to hold all of the electrolyte which would otherwise be contained in the reservoir 8. Under typical working conditions, all of the electrolyte can then be taken up by the separators and wick. However, it is useful to leave some space in the housing 2 and/or wick 6 to allow for increases in the volume of liquid in the cell should it take up water in humid atmospheres.

The wick 6 and the wick compression component 7 can take a number of different forms. In making an appropriate selection, the following factors should be taken into account:

Capillary action in the wick 6 is improved by compression up to a certain point. However, excess compression could lead to obstruction of the pores in the wick material;

Efficient electrolyte transfer between the wick 6 and the sensor stack 5 requires sufficient contact area between the wick 6 and the lowermost electrode or separator layer; and Ease of assembly with other sensor components.

In their most basic forms, the wick component 6 (in its uncompressed state) and the wick compression component 7 could both be cylindrical, the wick compression component 7 having a smaller diameter than that of the wick 6 prior to insertion into the wick compression component 7. However, cylindrical compression of the wick 6 along its entire length leads to a reduced cross-sectional area of its end facing the electrode stack 5. The embodiment shown in FIG. 1 therefore includes an improvement, in which a first portion of the wick 6 is cylindrically compressed, but an end portion adjacent the electrode stack 5 is subjected to a lesser degree of compression, thus retaining a greater cross-sectional area.

Figure 3B:
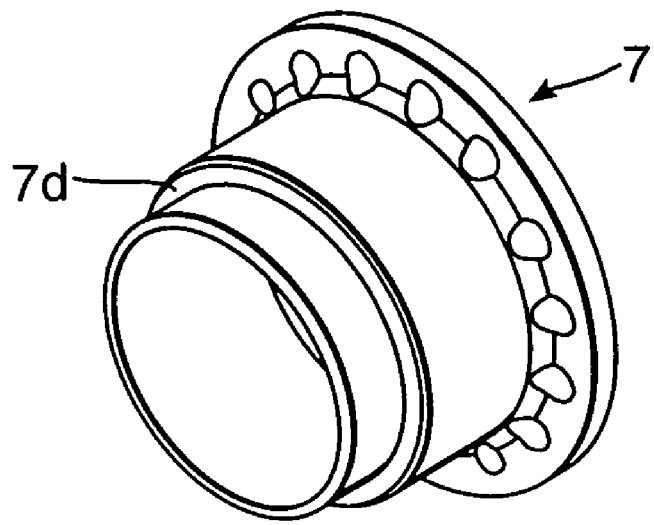

The wick compression component 7 and wick 6 used in the embodiment shown in FIG. 1 are shown in greater detail in FIGS. 3, 4 and 5. FIGS. 3a and 3b show the wick compression component 7 in perspective view from each end. It can be seen that the exterior profile of the component is quite different to that of its internal volume. This is shown in more detail in FIGS. 4a, 4b, 4c and 4d. The cross-sectional view of FIG. 4b shows the wick compression component 7 to have three distinct internal portions. The first, 7a, is located adjacent to the end of the component nearest the electrode assembly 5. The diameter of the internal volume decreases from $D_1$ to $D_2$ across volume 7a, the walls of which are shown as curved but may equivalently be straight, essentially forming a frustoconical volume. The second portion, 7b, lies immediately adjacent to volume 7a and is substantially frustoconical, the internal diameter decreasing from $D_2$ to $D_3$, which in this embodiment is the smallest diameter of the internal volume along the sensor axis. The third portion, 7c, completes the wick compression component 7 and may be substantially cylindrical or, as shown in FIG. 3b, frustoconical. The diameter increases from $D_3$ to $D_4$ at the end of the wick compression component 7 adjacent to the reservoir 8. In a cylindrical embodiment, the values of $D_3$ and $D_4$ are equal.

Figure 5A:
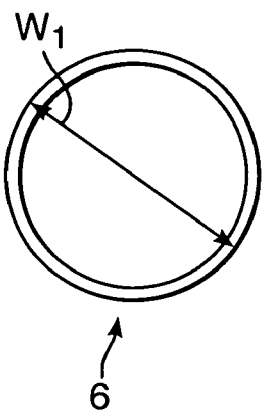
FIGS. 5a, 5b and 5c show respectively a plan view, a side view and a perspective view of a wick for use in a first embodiment of the present invention.
Figure 5B:
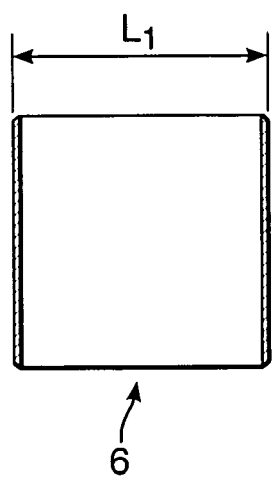
Figure 5C:
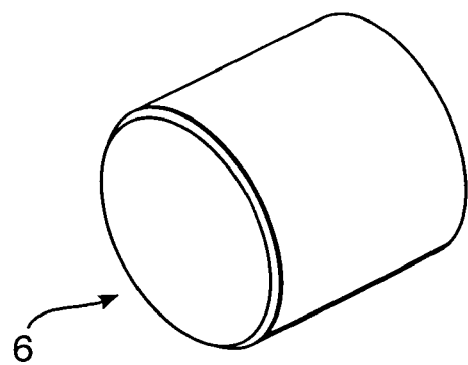

Thus, on insertion into wick compression component 7, a substantially cylindrical wick 6 (as shown in FIGS. 5a, 5b and 5c) is compressed by different degrees in each of portions 7a, 7b and 7c, resulting in a substantially cylindrical compressed wick but with increased diameter at one end.

Uncompressed, the wick 6 may for example have a diameter $W_1$ of 9.75±0.25 mm and a length, $L_1$, of 10.00±0.25 mm. Each end of the cylindrical wick may be bevelled in order to ease insertion into the wick compression component 7. The wick 6 is made of a fibrous material, such as polyolefin/polyester fibres. Material number XM-1907 manufactured by POREX™ has been found to be suitable for this purpose.

The minimum internal diameter $D_3$ of the wick compression component 7 may be approximately 8.1±0.1 mm. This is 83% of the wick diameter $W_1$, and therefore results in a 17% compression of the wick. This degree of compression has been found to optimise electrolyte transfer in wicks made of XM-1907.

On the exterior of the wick compression component 7, an annular flange 12 is provided around one end to support the electrode stack 5. Breather holes 12a are provided in the flange 12 to allow contact between electrolyte in the reservoir (prior to absorption by the wick 6) and the electrode assembly 5. This provides initial fast wetting of the electrodes and speeds activation of the cell. The diameter $D'_1$ of the flange 12 is selected to fully support the electrode stack 5.

The wick compression component 7 is also provided with a step feature 7d which divides a lower portion of reduced external diameter $D'_3$ from a region of greater external diameter $D'_2$. This enables the wick compression component 7 to fit into the reservoir 8 and be supported at step 7d by the upper sides of internal walls 8a of the housing. The wick compression component 7 is conveniently made of polyolefin and polystyrene (PPE), such as GE Noryl SE100x.

During manufacture, the wick 6 could be inserted into the wick compression component 7 such that the ends of the two components align flush with one another. However, it is found to be beneficial if the wick 6 extends out of the wick compression component 7 a small way at its end adjacent to the electrode stack 5. It is important to ensure that on assembly the wick cannot be pushed down below the upper edge of the wick compression component 7, since this could result in less efficient or entire loss of electrolyte transport from the wick 6 into the separators 16, 17, 18. The shape of the wick compression component 7 and the positioning of the wick helps to minimise such a risk and maintain good contact to the separators. This arrangement also provides some flexibility in the compression of the electrode stack when the sensor housing is closed. However, the perimeter of the holder (flange 12) is still able to provide a firm base against which to build the electrode stack 5.

The larger capillary diameters in the upper section of the wick 6 which might be expected to result from allowing this expansion do not compromise the overall electrolyte transport because the separators forming part of the electrode stack 5 are chosen to have a greater affinity (in terms of their physical properties) for the electrolyte than that of the wick. Once the wick 6 has transported the electrolyte from the reservoir 8 of the bottom of the cell to the upper regions of the wick 6, the capillary attraction offered by the separator components takes over and provides the wicking force up to the electrodes.

Figure 6A:
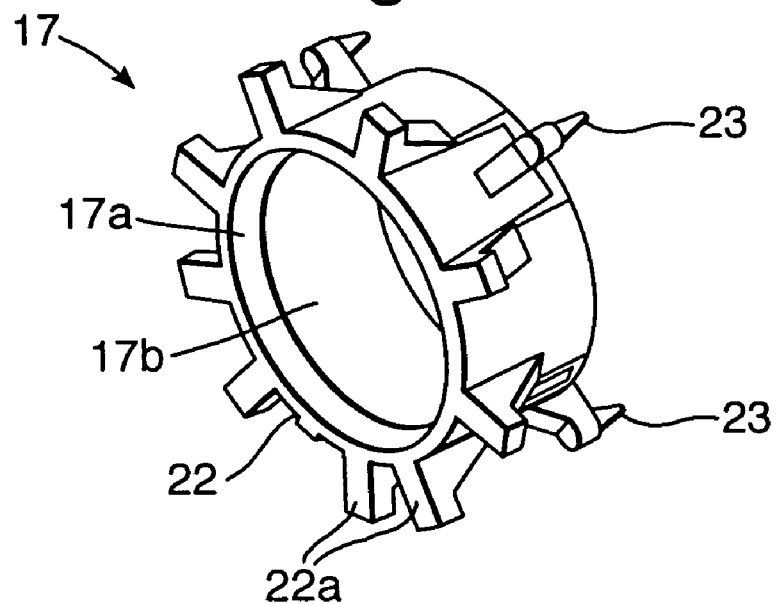
FIGS. 6a and 6b show perspective views of a second wick compression component for use in a second embodiment of the present invention.
Figure 6B:
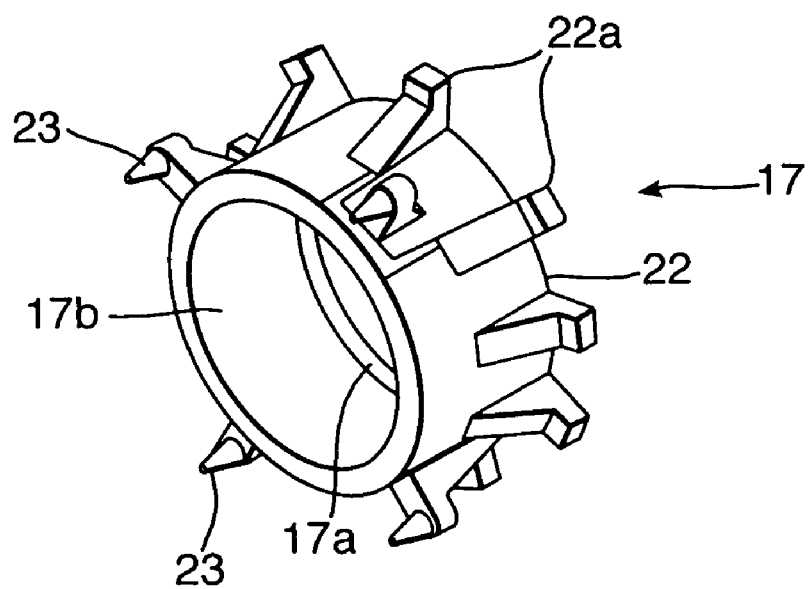
Figure 7D:
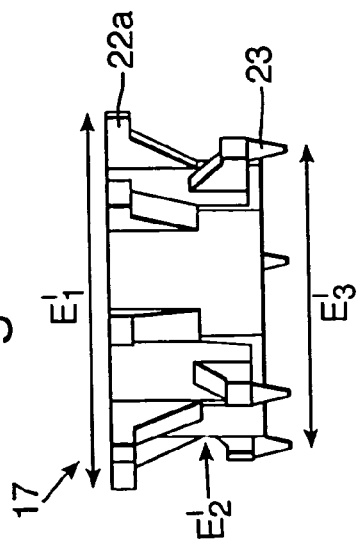
FIGS. 7a, 7b, 7c and 7d show respectively a plan view, a cross-section, a view from underneath and a side view of the wick compression component depicted in FIGS. 6a and 6b.
Figure 7C:
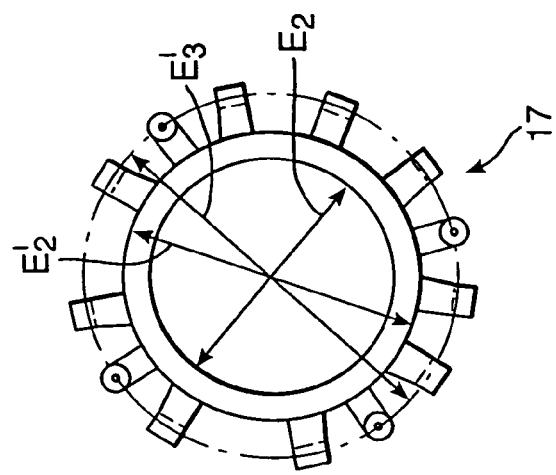
Figure 7B:
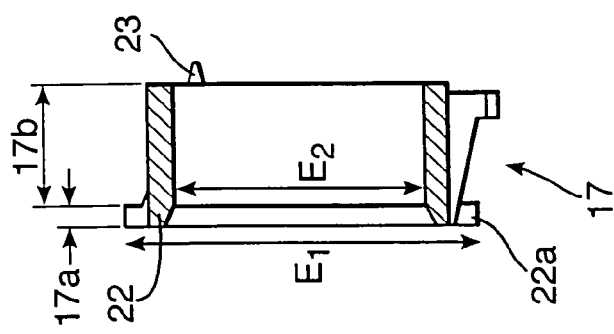
Figure 7A:
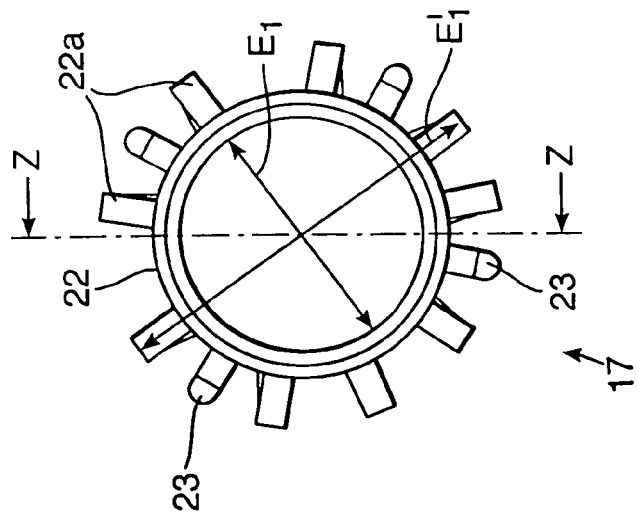

FIGS. 6a and 6b show an alternative wick compression component 17 which may be used in a second embodiment. In this example, a simpler internal profile is provided with a first frustoconical section 17a over which the internal diameter decreases from $E_1$ to $E_2$ (see FIG. 7b) and a second cylindrical section 17b of internal diameter $E_2$.

The wick compression component 17 is provided with external lugs 22a attached to rim 22 which support the electrode assembly 5 in the same way as flange 12 of wick compression component 7. The spaces between lugs 22a perform the function of the breather holes 12a. Four locator pins 23 are provided to assist in locating the base of wick compression component 17 within the sensor housing.

Figure 8:
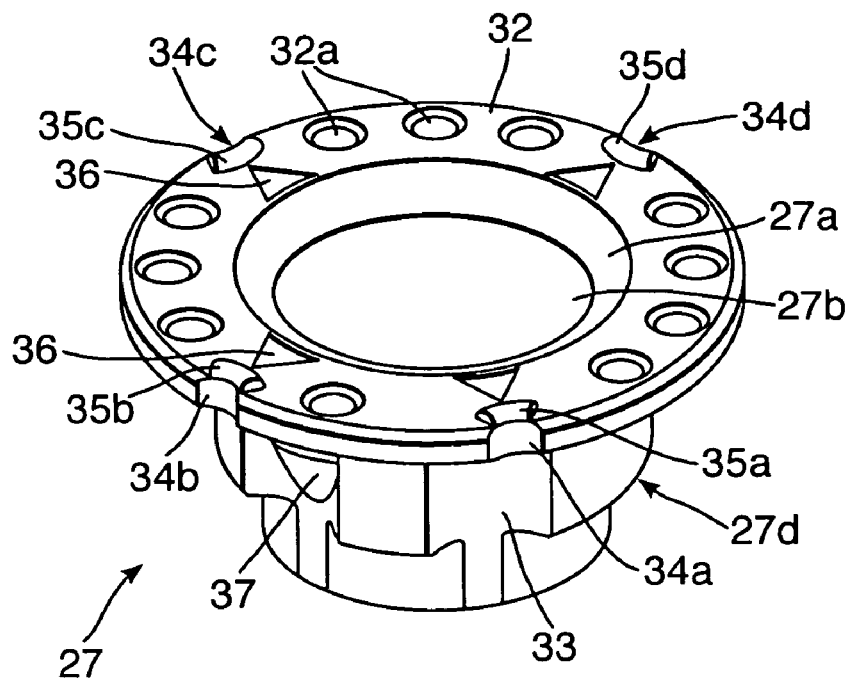
FIG. 8 shows a perspective view of a third wick compression component for use in a third embodiment of the present invention.
Figure 9:
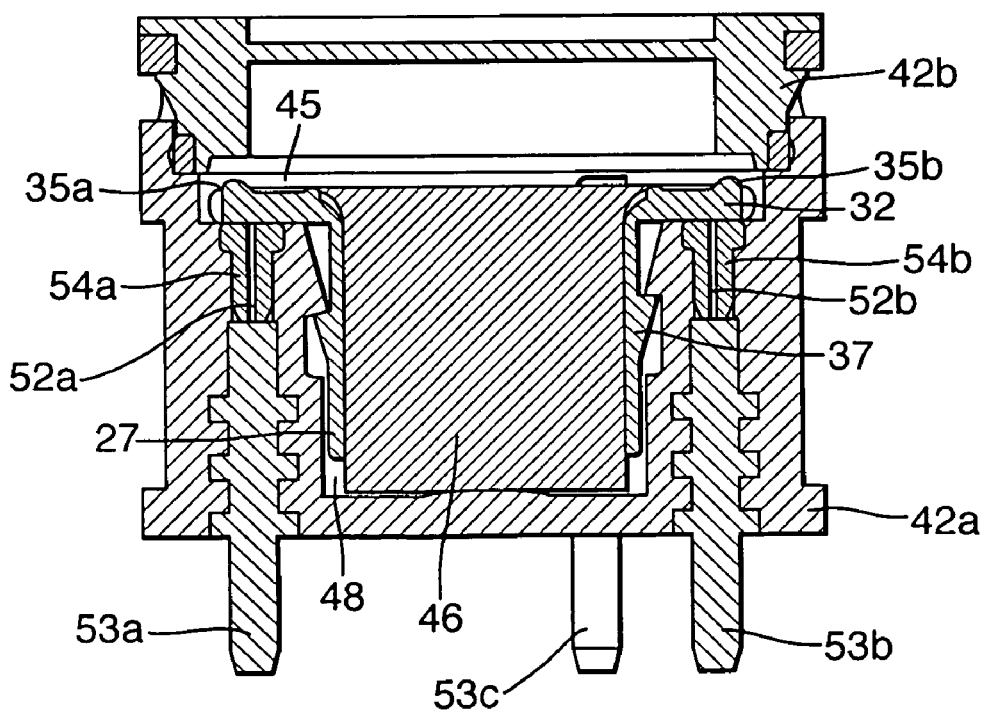
FIG. 9 depicts a cross-section through a gas sensor in accordance with the third embodiment of the present invention.

FIG. 8 shows a further alternative example of a wick compression component 27 for use in a third embodiment which is shown in cross-section in FIG. 9.

The wick compression component 27 has an internal volume made up of two portions 27a and 27b similar to those of wick compression component 17 (FIGS. 6 and 7). Externally, the component is provided with a flange 32 and breather holes 32a equivalent to flange 12 and breather holes 12a in the first embodiment. Similarly, the wick compression component 27 is provided with a step 27d which locates the component inside the reservoir 8. These features have already been described above with respect to the first and second embodiments. However, the wick compression component 27 is further provided with a number of additional features.

The body of the wick compression component 27 is provided on its outside with a number of recesses 33 which are positioned around its periphery to assist in guiding the wick compression component 27 in a parallel motion into the sensor housing 42 (FIG. 8). Snap-fit features may also be provided in the form of barbs 37 on the exterior of wick compression component 27 and corresponding shoulders on the interior walls of housing base 42a. These cooperate to perform three functions. Firstly, the wick compression component 27 and enclosed wick 46 are securely retrained to create a stable platform on which to build the electrode stack 45; secondly, a reliable and constant compression is exerted on the wick 46 and thirdly sealing of the current collectors is improved.

As previously mentioned, current collectors are provided to connect each electrode with an external circuit. Typically, the current collectors themselves are in the form of thin, flexible lengths of wire which interleave with the components in the electrode stack 45 (see FIG. 2). FIG. 9 shows two current collectors 52a and 52b which electrically connect their respective electrodes with connection pins 53a and 53b. A third connection pin 53c can also be seen extending out of the base of the sensor housing 42. The electrode pins are formed integrally with the housing base 42a, extending through, and encased by, the wall of the housing. The current collectors contact the connection pins at their internal ends located within recesses in the housing 42. In order to prevent leakage of electrolyte, the current collectors 52a and 52b are each provided with a seal component 54a and 54b respectively, through which the current collector extends and which substantially fills the recesses in the housing. The seal components 54a and 54b are made of a resilient material and are described more fully in WO2005/017518 for example. When in position, the wick compression component 27 also exerts a force on the end of each seal component 54a and 54b, causing it to expand laterally and thus create a seal between the current collector and the housing. This ensures a reliable, parallel seal across the face of the sealing components 54a and 54b, preventing slippage which could lead to electrolyte leakage.

The current collectors 52 extend from the seal components 54 around the edge of flange 32 on the wick compression component 27 and into the electrode stack 45. Protrusions 35a, 35b, 35c and 35d are provided on the wick compression component 27 adjacent to the edge of flange 32 to provide guidance for the current collectors. Each current collector is formed around its respective protrusion 35 which positions it for contact with its respective electrode. Since each electrode is at a different height in the stack, the protrusions 35 are each slightly different in profile and height so as to form the current collectors to their individual positions. This enables the current collectors to be positioned reliably, without damage to the electrodes or trapping in seal joints as is a current issue.

Further, this technique lends itself to automated assembly whereas existing techniques are notoriously difficult for manual assembly and are generally not even considered for automation.

Cut-outs 34a, 34b, 34c and 34d in the flange perimeter provide clearance and location for the passage of the current collectors 52a and 52b and again assist in the reduction of damage to the current collectors on forming of the delicate wire. Finally, the flange 32 may further be provided with a number of symbols such as triangles 36 which allow an automated optical recognition system to recognise the orientation of the part.

In summary, the above described embodiments illustrate a number of ways in which a compressed wick can be used to enhance the transport of electrolyte to the sensor assembly. Test results have shown that, compared to conventional sensors, the response speed is maintained for a much a longer period of time. Further, the wick compression component can carry out a number of auxiliary functions including support for the electrodes, positioning of the wick and seal compression amongst others.

We claim:

1. An electrochemical gas sensor comprising an electrode assembly, including a catalytic sensing electrode and a counter electrode, mounted inside a housing provided with at least one gas entrance, a reservoir for containing electrolyte in use, a compressible wick for supplying the electrode assembly with electrolyte and a wick compression component, wherein a first end of the wick extends into the reservoir and a second end of the wick contacts the electrode assembly, and the wick compression component compresses the wick in a direction substantially radial to an axis joining its first and second ends.

2. An electrochemical gas sensor according to claim 1 wherein the wick compression component has a longitudinal axis extending between a first open end adjacent to the reservoir and a second open end adjacent to the electrode assembly, and defines an internal volume into which the wick is placed in use, wherein the cross-sectional area of the internal volume in a plane perpendicular to the longitudinal axis is less than the cross-sectional area of the wick prior to its insertion into the wick compression component at least one point along the longitudinal axis, so that the internal walls exert a compressive force on the wick.

3. An electrochemical gas sensor according to claim 2 wherein the internal volume defined by the wick compression component has a substantially circular cross section.

4. An electrochemical gas sensor according to claim 2 wherein at least a first portion of the internal volume defined by the wick compression component is substantially cylindrical, at least a first part of the wick compression component having parallel-sided internal walls.

5. An electrochemical gas sensor according to claim 2 wherein at least a first portion of the internal volume defined by the wick compression component is substantially frusto-conical, the wick compression component having a first part which has an internal width dimension which is larger at its first end than at its second end, the first end located towards the reservoir.

6. An electrochemical gas sensor according to claim 4 wherein a second portion of the internal volume defined by the wick compression component adjacent to the second end of the wick compression component, has a cross-sectional area larger than that of the first portion.

7. An electrochemical gas sensor according to claim 6 wherein the second portion is substantially frustoconical, the wick compression component having a second part which has an internal diameter which is smaller at its first end than at its second end, the first end located toward the reservoir.

8. An electrochemical gas sensor according to claim 2 wherein the wick compression component has an internal width dimension at least one point along the longitudinal axis which is 17% less than the width of the wick prior to insertion.

9. An electrochemical gas sensor according to claim 1 wherein, prior to insertion into the wick compression component, the wick is substantially cylindrical.

10. An electrochemical gas sensor according to claim 9 wherein the wick compression component defines a first cylindrical internal volume in accordance with claim 5, and the internal diameter of the cylinder is 17% less than the diameter of the wick prior to insertion.

11. An electrochemical gas sensor according to claim 1 wherein the wick has a capacity for holding electrolyte at least equal to that of the reservoir.

12. An electrochemical gas sensor according to claim 1 wherein the wick compression component further comprises a surface for supporting the electrode assembly inside the housing, the wick compression component thereby contacting at least a portion of the electrode assembly.

13. An electrochemical gas sensor according to claim 12 wherein the second open end of the wick compression component provides the electrode assembly support surface.

14. An electrochemical gas sensor according to claim 12 wherein the wick compression component is further provided with a flange around its second open end, the flange providing the electrode assembly support surface.

15. An electrochemical gas sensor according to claim 2 wherein the second end of the wick is adapted to be substantially flush with the second end of the wick compression component.

16. An electrochemical gas sensor according to claim 2 wherein the wick is adapted to extend out of the second end of the wick compression component to contact the electrode assembly.

17. An electrochemical gas sensor according to claim 1 wherein the wick comprises a porous material.

18. An electrochemical gas sensor according to claim 1 wherein the wick comprises a fibrous material.

19. An electrochemical gas sensor according to claim 18 wherein the fibres of the wick material are orientated substantially parallel to the axis joining the first and second ends of the wick.

20. An electrochemical gas sensor according to claim 18 wherein the fibres define elongate, substantially parallel pores aligned with the fibres.

21. An electrochemical gas sensor according to claim 1 wherein the wick comprises polyethylene.

22. An electrochemical gas sensor according to claim 1 wherein the housing comprises a base and a lid.

23. An electrochemical gas sensor according to claim 1 wherein the reservoir is defined by interior walls of the housing.

24. An electrochemical gas sensor according to claim 1 wherein the electrode assembly further comprises a reference electrode.

25. An electrochemical gas sensor according to claim 1 wherein the electrode assembly further comprises at least one separator, which supplies electrolyte from the wick to electrodes in the electrode assembly.

26. An electrochemical gas sensor according to claim 25 wherein the separator is made of a material which has a greater affinity for the electrolyte than does the wick material.

27. An electrochemical gas sensor according to claim 1 further comprising at least one current collector for connecting the electrode assembly with a circuit, the wick compression component further comprising a guide protrusion for the or each current collector, around which the or each current collector is formed to achieve contact with an electrode in the electrode assembly.

28. An electrochemical gas sensor according to claim 1 further comprising at least one current collector for connecting the electrode assembly with a circuit, the at least one current collector being provided with a compliant seal component through which the current collector extends and which creates a seal between the current collector and the housing to prevent egress of electrolyte.

29. An electrochemical gas sensor according to claim 28 wherein the wick compression component contacts the or each compliant seal component so as to exert a compressive force and thereby create the seal.

30. A method of manufacturing an electrochemical sensor comprising the steps of:
(A) compressing a wick having first and second ends in a direction substantially radial to an axis joining its first and second ends;
(B) positioning the compressed wick such that the first end of the wick extends into a reservoir for containing electrolyte in use and the second end of the wick contacts an electrode assembly, including a catalytic sensing electrode and a counter electrode, inside a housing, the housing being provided with at least one gas entrance; and
(C) at least partially filling the reservoir with electrolyte such that the wick supplies the electrode with electrolyte from the reservoir.

31. A method according to claim 30 wherein step A comprises the steps of:
(A1) providing a wick compression component having a longitudinal axis extending between a first open end and a second open end, and defining an internal volume, wherein the cross-sectional area of the internal volume in a plane perpendicular to the longitudinal axis is less than the cross-sectional area of the uncompressed wick at least one point along the longitudinal axis; and
(A2) inserting the wick into the volume defined by the wick compression component, thereby exerting a compressive force on the wick in a substantially radial direction.

32. A method according to claim 31 wherein, in step (A2), the wick is inserted such that its second end extends out of the second end of the wick compression component.

33. A method according to claim 30 wherein step (B) comprises the steps of:
(B1) positioning the compressed wick such that its first end extends into the reservoir, the reservoir being provided in a base component of the housing;
(B2) placing the electrode assembly on the compressed wick such that the electrode assembly is supported by the wick; and
(B3) closing the housing by means of a lid component of the housing.

34. A method according to claim 33 wherein the wick is compressed by inserting it into a wick compression component.

35. A method according to claim 34 wherein in step (B2), the electrode assembly is placed on, and supported by, the wick compression component.

* * * * *